(12) United States Patent
Nishigaki et al.

(10) Patent No.: US 6,331,645 B2
(45) Date of Patent: Dec. 18, 2001

(54) PROCESS FOR PREPARING POWDERY ALKYL SULFATES

(75) Inventors: Futoshi Nishigaki; Osamu Tabata, both of Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/725,250

(22) Filed: Nov. 29, 2000

(30) Foreign Application Priority Data

Dec. 1, 1999 (JP) .................................................. 11-342190

(51) Int. Cl.$^7$ .................................................. C07C 303/00
(52) U.S. Cl. .................................................. 558/39
(58) Field of Search .................................................. 558/39

(56) References Cited

FOREIGN PATENT DOCUMENTS

| 0 572 957 | 12/1993 | (EP) . |
| 52-46025 | 4/1977 | (JP) . |

*Primary Examiner*—Joseph K. McKane
*Assistant Examiner*—Joseph Murray
(74) *Attorney, Agent, or Firm*—Oblon, Spivak, McClelland, Maier & Neustadt, P.C.

(57) ABSTRACT

A process for preparing a powdery alkyl sulfate, comprising drying aqueous slurry having a solid content of 60 to 85% by weight and containing an alkyl sulfate and an alkali metal carbonate in a ratio of 0.05 to 10 parts by weight of the alkali metal carbonate based on 100 parts by weight of the alkyl sulfate. This process is capable of stably preparing a powdery alkyl sulfate without deteriorating the quality of aqueous slurry of an alkyl sulfate and powder obtainable from the aqueous slurry.

3 Claims, No Drawings

PROCESS FOR PREPARING POWDERY ALKYL SULFATES

BACKGROUND OF THE INVENTION

1. Field of the Invention

The present invention relates to a process for preparing a powdery alkyl sulfate. More specifically, the present invention relates to a process for preparing a powdery alkyl sulfate which can be suitably used for laundry detergents, toothpaste additives, detergents and the like.

2. Discussion of the Related Art

As processes for preparing a powder or granulated product of an alkyl sulfate, there have been known a process comprising spray-drying aqueous slurry of an alkyl sulfate, the solid content of which is 60 to 80% by weight, by utilizing the minimum value of the viscosity of the aqueous slurry (Japanese Patent Laid-Open No. Sho 54-106428); a process comprising vacuum-thin-film drying aqueous slurry of an anionic surfactant such as an alkyl sulfate, the solid content of which is 60 to 80% by weight (Japanese Patent Laid-Open No. Hei 5-331496); a process for preparing a powder by controlling the water content of aqueous slurry of an anionic surfactant such as an alkyl sulfate to a very low level (Japanese Patent Laid-Open No. Hei 11-5999), and the like.

In those processes, while the solid content is adjusted to 60 to 80% by weight in order to lower the viscosity of the aqueous slurry of the alkyl sulfate, the viscosity of the aqueous slurry is remarkably high as compared to an aqueous solution of an alkyl sulfate. Therefore, there is a necessity in those processes to maintain the aqueous slurry at high temperatures in order to lower its viscosity and improve the operability of the aqueous slurry.

However, there are some defects in those processes that the aqueous slurry tends to be decomposed, and its pH is lowered when this aqueous slurry is kept at high temperatures, so that the quality before or after drying is deteriorated, thereby making it difficult to store the product for a long period of time.

An object of the present invention is to provide a process capable of stably preparing a powdery alkyl sulfate without deteriorating the quality of aqueous slurry of an alkyl sulfate and powder obtainable from the aqueous slurry.

The above and other objects of the present invention will be apparent from the following description.

SUMMARY OF THE INVENTION

According to the present invention, there is provided a process for preparing a powdery alkyl sulfate, comprising drying aqueous slurry having a solid content of 60 to 85% by weight and containing an alkyl sulfate and an alkali metal carbonate in a ratio of 0.05 to 10 parts by weight of the alkali metal carbonate based on 100 parts by weight of the alkyl sulfate.

DETAILED DESCRIPTION OF THE INVENTION

Examples of an alkyl sulfate include the compound represented by the formula (I):

$$R^1\text{—}OSO_3M \quad (I)$$

wherein $R^1$ is a linear or branched alkyl group or alkenyl group having 8 to 18 carbon atoms; and M is an alkali metal atom or an alkanol-substituted or unsubstituted ammonium group. These compounds can be used alone or in admixture thereof The alkali metal atom includes sodium atom, potassium atom and the like. In addition, the alkanol includes an alkanol having 1 to 3 carbon atoms, preferably 1 or 2 carbon atoms such as methanol and ethanol.

Examples of the alkali metal carbonates include sodium carbonate, potassium carbonate, and the like. Among them, sodium carbonate can be preferably used.

The process for preparing aqueous slurry of an alkyl sulfate having a solid content of 60 to 85% by weight from an alkyl sulfate includes, for instance, a process comprising previously condensing aqueous slurry of the alkyl sulfate having a solid content of not more than 40% by weight; a process for directly preparing aqueous slurry having a high solid content by utilizing the minimum value of the viscosity of the aqueous slurry of the alkyl sulfate, and the like, and any of those processes can be employed in the present invention.

The solid content as referred to in the present specification means ingredients other than a solvent contained in the aqueous slurry.

The solid content of the aqueous slurry of the alkyl sulfate is 60 to 85% by weight, preferably 65 to 80% by weight, from the viewpoint of preventing the lowering of operability due to gelling.

In addition, it is desired that pH of the aqueous slurry of the alkyl sulfate is not less than 7, preferably not less than 7.5, from the viewpoint of preventing the decomposition of the alkali metal carbonate added.

It is desired that the amount of the alkali metal carbonate added to the aqueous slurry of the alkyl sulfate having the above-mentioned solid content is 0.05 to 10 parts by weight, preferably 0.1 to 5 parts by weight based on 100 parts by weight of the alkyl sulfate, from the viewpoints of suppressing the foaming during addition and maintaining the alkyl sulfate at a high concentration.

As pH buffer, phosphate, citrate, or the like may be contained in the aqueous slurry of the alkyl sulfate. It is preferable that the amount of the buffer is usually not more than 1 part by weight, more preferably not more than 0.5 parts by weight based on 100 parts by weight of the alkyl sulfate.

In addition, it is desired that the temperature of the aqueous slurry of the alkyl sulfate is 50° to 140° C., preferably 60° to 100° C. when an alkali metal carbonate is added to the aqueous slurry, from the viewpoints of being capable of easily mixing the aqueous slurry without exceedingly increasing the viscosity, improving the operability, and suppressing the decomposition of the aqueous slurry.

After the alkali metal carbonate is added to the aqueous slurry of the alkyl sulfate, the aqueous slurry is dried.

When the aqueous slurry is dried, it is preferable to use a rotary thin-film evaporator, from the viewpoints of facilities and energy efficiency.

The rotary thin-film evaporator includes, for instance, evaporators described in "Kagaku Souchi Hyakka Jiten (Encyclopedia for Chemical Apparatus)" edited by Kagaku Souchi Hyakka Jiten Henshu Iinkai [published by K.K. Kagaku Kogyo, 1971, 103–104], and the like. Among the evaporators, centrifugal thin-film evaporators equipped with rotating blades can be favorably used, because a thin film of an aqueous solution of an alkyl sulfate or aqueous slurry of an alkyl sulfate can be formed by centrifugal force of the rotating blades.

Among the rotary thin-film evaporators, a vertical rotary thin-film evaporator is preferable, from the viewpoint that the final powdery product can be easily discharged by gravitational force. The vertical rotary thin-film evaporator includes Kontro, Sevcon [hereinabove commercially available from Hitachi LTD., trade names]; EVAOLATOR, Hi-EVAOLATOR [hereinabove commercially available from K.K. Sakura Seisakusho, trade names], LUWA Distillator [commercially available from LUWA (Switzerland), trade name], Film Evaporator WIPRENE [commercially available from Shinko Pantec Co., Ltd., trade name], and the like.

Next, embodiments where the rotary thin-film evaporator is used as an evaporator will be explained.

First, aqueous slurry of an alkyl sulfate is added to a rotary thin-film evaporator. During the addition, it is desired that the temperature of the aqueous slurry of the alkyl sulfate is 50° to 140° C., preferably 60° to 100° C., from the viewpoints of improving the operability without exceedingly increasing the viscosity, suppressing the decomposition of the alkyl sulfate and the alkali metal carbonate, and maintaining its quality.

It is desirable that a heat transfer inner wall surface of the rotary thin-film evaporator is appropriately heated, from the viewpoint of increasing drying efficiency. The heat transfer inner wall surface can be heated by, for instance, introducing heated steam or hot water into its heating jacket or the like. In this case, it is desired that the temperature of the beat transfer inner wall surface is 70° to 140° C., preferably 80° to 120° C., from the viewpoints of increasing drying efficiency, and preventing decomposition and change of color tone of the alkyl sulfate. The temperature of the heat transfer inner wall surface can be determined by bringing a thermometer into contact with the back side of the inner wall.

It is desired that the rotational speed of the rotating blade of the rotary thin-film evaporator is not less than 5 m/s, preferably not less than 8 m/s as a tip end peripheral speed of the rotating blade, from the viewpoint of increasing drying efficiency, and that the rotational speed is not more than 20 m/s, preferably not more than 18 m/s, from the viewpoint of improving the operability. Accordingly, in consideration of the above viewpoints, it is desired that the rotational speed is 5 to 20 m/s, preferably 8 to 18 m/s.

It is desired that the pressure inside the rotary thin-film evaporator is not more than 26664 Pa (about 200 Torr), preferably 6666 to 13332 Pa (about 50 to 100 Torr), from the viewpoint of increasing drying efficiency.

The feeding rate of the aqueous slurry can be appropriately adjusted depending upon the drying conditions of the aqueous slurry of the alkyl sulfate. The feeding rate is preferably not more than 70 kg/m²·h, more preferably not more than 60 kg/m²·h, from the viewpoint of increasing drying efficiency.

As described above, the powdery alkyl sulfate can be easily prepared by drying the aqueous slurry of the alkyl sulfate, for instance, to a water content of not more than 4% by weight.

EXAMPLES

Example 1

To 100 parts by weight of a mixture of sodium linear alkyl sulfates having different chain lengths, composed of 65% by weight of one having a linear alkyl moiety of 12 carbon atoms; 30% by weight of one having a linear alkyl moiety of 14 carbon atoms; and 5% by weight of one having a linear alkyl moiety of 16 carbon atoms, were added 0.3 parts by weight of sodium phosphate and 0.2 parts by weight of sodium carbonate, and its solid content was adjusted to 71% by weight, to give aqueous slurry.

Next, the resulting aqueous slurry was stored at 90° C., and its pH was examined with the passage of time. The pH was determined with an aqueous solution prepared by diluting the aqueous slurry with water to a solid content of 1% by weight. The results are shown in Table 1.

Example 2

The same procedures as in Example 1 were carried out except that the amount of sodium carbonate was changed to 4.5 parts by weight, and the change of pH was examined with the passage of time in the same manner as in Example 1. The results are shown in Table 1.

Comparative Example 1

The same procedures as in Example 1 were carried out except that the amount of sodium carbonate was not added at all, and the change of pH was examined with the passage of time in the same manner as in Example 1. The results are shown in Table 1.

TABLE 1

| Example No. | Change of pH with Passage of Time | | | |
|---|---|---|---|---|
| | Initial | After 5 h | After 10 h | After 15 h |
| 1 | 9.5 | 9.5 | 9.5 | 9.4 |
| 2 | 9.5 | 9.5 | 9.5 | 9.5 |
| Comp. Example 1 | 9.5 | 9.0 | 8.4 | 7.5 |

It can be seen from the results shown in Table 1 that the change of pH of the powders obtained in Examples 1 and 2 is small with the passage of time since sodium carbonate is added to the alkyl sulfates, so that the aqueous slurry of the alkyl sulfate is excellent in storage stability.

Example 3

The aqueous slurry obtained in Example 1 was fed at 70° C. at a feeding rate of 50 kg/m²·h, and powdered by using a rotary thin-film evaporator having a heat transfer area of 0.3 m², commercially available from Hitachi LTD., under the trade name: SEVCON. During powdering, the temperature of the heat transfer inner wall of the evaporator was adjusted to 110° C., the degree of vacuum, 9310 Pa (about 70 Torr), and the rotational speed of the rotating blades, 1100 rpm (tip end peripheral speed: 8.9 m/s).

The powder was added to water so that the concentration of the resulting powdery alkyl sulfate became 1% by weight, and the change of pH was examined with the passage of time at 80° C. The results are shown in Table 2.

Example 4

The same procedures as in Example 3 were carried out except that the same one as that used in Example 2 was used as aqueous slurry, and the change of pH was examined with the passage of time in the same manner as in Example 3. The results are shown in Table 2.

TABLE 2

| Example No. | Water Content (%) | Change of pH with Passage of Time | | | |
|---|---|---|---|---|---|
| | | Initial | After 2 h | After 4 h | After 6 h |
| 3 | 1.5 | 9.5 | 9.5 | 9.5 | 9.3 |
| 4 | 1.5 | 9.5 | 9.5 | 9.5 | 9.4 |
| Comp. Example 2 | 1.6 | 9.5 | 9.2 | 6.8 | 3.7 |

It can be seen from the results shown in Table 2 that the change in pH of the powders obtained in Examples 3 and 4 is small with the passage of time since sodium carbonate is added to the aqueous slurry of the alkyl sulfate, so that the powder is excellent in storage stability.

Having described above, according to the process of the present invention, not only aqueous slurry of the alkyl sulfate but also powder or granule thereof, which have a small change of pH with the passage of time and are excellent in storage stability.

What is claimed is:

1. A process for preparing a powdery alkyl sulfate, comprising drying aqueous slurry having a solid content of 60 to 85% by weight and containing an alkyl sulfate and an alkali metal carbonate in a ratio of 0.05 to 10 parts by weight of the alkali metal carbonate based on 100 parts by weight of the alkyl sulfate.

2. The process according to claim 1, wherein the aqueous slurry is dried by using a rotary thin-film evaporator.

3. The process according to claim 1, wherein the alkali metal carbonate is sodium carbonate.

* * * * *